United States Patent
Eiskant et al.

(10) Patent No.: US 7,267,246 B2
(45) Date of Patent: *Sep. 11, 2007

(54) STERILE CONTAINER AND LID FOR A STERILE CONTAINER

(75) Inventors: Karl-Heinz Eiskant, Tuttlingen (DE); Mariana Jakab, Tuttlingen (DE); Friedrich-Wilhelm Oertmann, Tuttlingen (DE); Torsten Renner, Eisenberg (DE); Stefan Schuster, Villingen-Schwenningen (DE); Wolfgang Schwanke, Rietheim-Weilheim (DE)

(73) Assignee: Aesculap AG & Co. KG, Tuttlingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/363,593

(22) Filed: Feb. 27, 2006

(65) Prior Publication Data

US 2006/0151509 A1    Jul. 13, 2006

Related U.S. Application Data

(63) Continuation of application No. 10/281,097, filed on Oct. 25, 2002, now Pat. No. 7,036,678.

(30) Foreign Application Priority Data

Aug. 27, 2002   (DE) .......................... 202 13 526 U

(51) Int. Cl.
    *B65D 39/00*   (2006.01)
(52) U.S. Cl. .................. 220/782; 220/795; 220/792; 220/324; 206/370
(58) Field of Classification Search ............... 220/324, 220/378, 780–795, 804, 833; 206/370
See application file for complete search history.

(56) References Cited

U.S. PATENT DOCUMENTS

| 1,011,976 | A | 12/1911 | Lithgow et al. |
| 2,071,881 | A | 2/1937 | Krause et al. |
| 3,524,564 | A | 8/1970 | Schurman |
| 3,531,013 | A | 9/1970 | Hammes |
| 4,034,889 | A | 7/1977 | Hammes et al. |

(Continued)

FOREIGN PATENT DOCUMENTS

DE           31 10 749           1/1982

(Continued)

OTHER PUBLICATIONS

Aesculap AG & Co. KG catalog entitled "Sterilcontainer System", May 2000.

*Primary Examiner*—Anthony D. Stashick
*Assistant Examiner*—James Smalley
(74) *Attorney, Agent, or Firm*—Lipsitz & McAllister LLC

(57) ABSTRACT

A lid for closing a sterile receptacle is provided. The receptacle is formed by a container bottom and container walls and defines a holding space. The lid comprises an angular cover plate which has a plurality of lid corners and closes the holding space in a closure position, such that it can be quickly and securely mounted on the receptacle and transferred to the closure position. A mounting aid is provided for mounting the lid on the receptacle. The mounting aid includes a plurality of mounting aid elements that each overlap at least one container wall at least partly in the closure position.

20 Claims, 3 Drawing Sheets

U.S. PATENT DOCUMENTS

| | | |
|---|---|---|
| 4,293,079 A | 10/1981 | Lytle |
| 4,412,630 A | 11/1983 | Daenen |
| 4,457,447 A | 7/1984 | Kirkis |
| 4,796,778 A | 1/1989 | Häbig et al. |
| 5,103,993 A | 4/1992 | Bingisser |
| 5,366,104 A | 11/1994 | Armstrong |
| 5,540,901 A | 7/1996 | Riley |
| 5,662,223 A | 9/1997 | Sylegård |
| 5,736,043 A | 4/1998 | Nichols et al. |
| 5,860,550 A | 1/1999 | Miller et al. |
| 5,925,247 A | 7/1999 | Huebbel |
| 6,142,332 A | 11/2000 | Ferrara |
| 6,352,170 B1 | 3/2002 | Brown et al. |
| 6,620,390 B1 | 9/2003 | Wagner |
| 6,622,871 B2 | 9/2003 | Gabele et al. |

FOREIGN PATENT DOCUMENTS

| | | |
|---|---|---|
| DE | 33 02 146 | 7/1984 |
| DE | 37 10 049 | 10/1988 |
| DE | 297 20 450 | 2/1998 |
| DE | 298 12 996 | 11/1998 |
| DE | 197 53 671 | 6/1999 |
| WO | 00/04933 | 2/2000 |

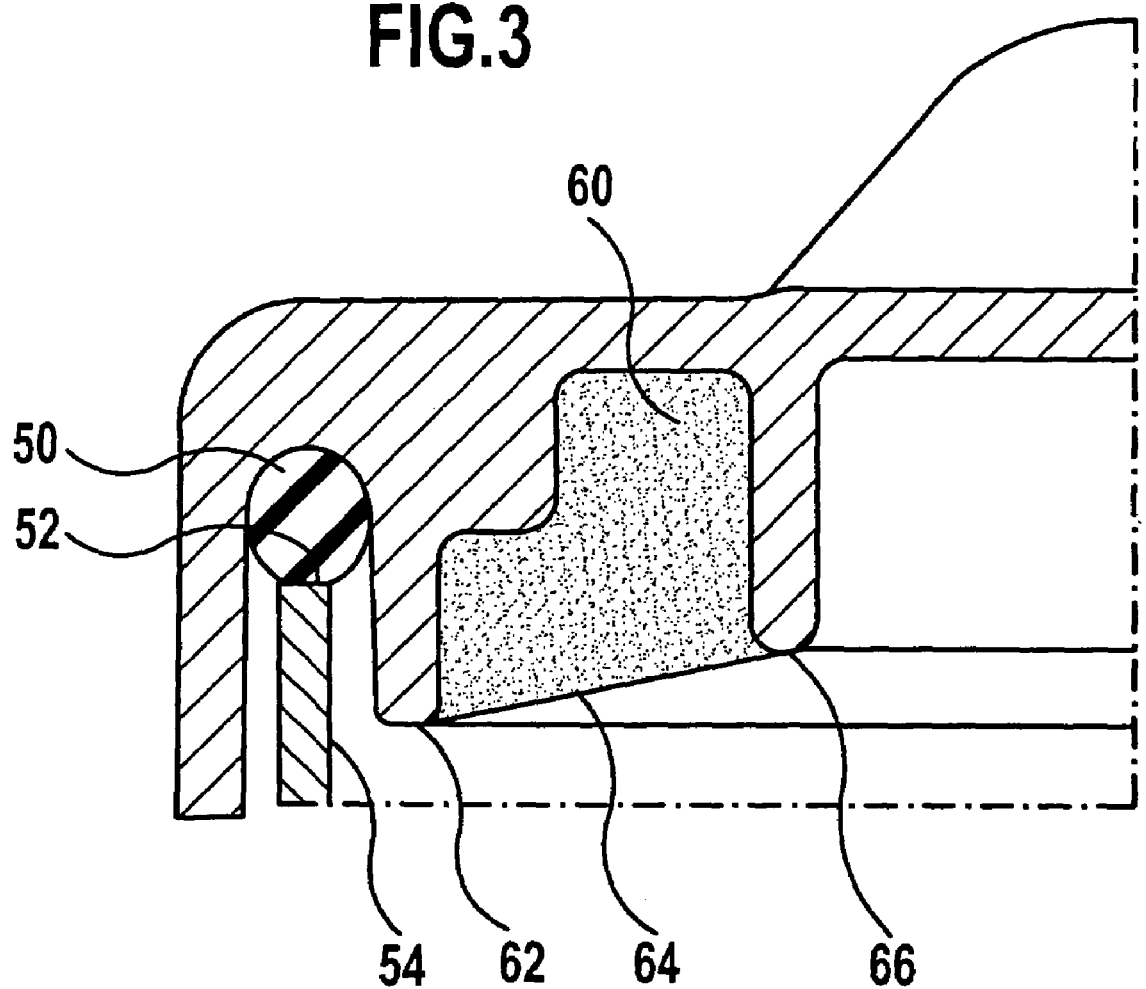

STERILE CONTAINER AND LID FOR A STERILE CONTAINER

This application is a continuation of U.S. patent application Ser. No. 10/281,097filed on Oct. 25, 2002, now U.S. Pat. No. 7,036,678 which claims the benefit of German utility model application No. 202 13 526.8 filed on Aug. 27, 2002, which is incorporated herein by reference in its entirety and for all purposes.

BACKGROUND OF THE INVENTION

The invention relates to a lid for closing a receptacle, which is formed by a container bottom and container walls and defines a holding space, of a sterile container which comprises the lid and which is developed in particular for holding surgical instruments or material and preserving the latter in a sterile state, wherein the lid comprises an angular cover plate which has a plurality of lid corners and closes the holding space in a closure position.

The invention also relates to a sterile container, in particular for holding surgical instruments or material and receptacle, which is formed by a container bottom and container walls and defines a holding space, and a lid for closing the receptacle.

A sterile container of the type initially described is used in order, for example, to sterilize surgical instruments or material in a sterilizing unit and preserve the latter following the sterilizing operation in the sterile container without having to remove the cover from the receptacle following sterilization.

In order that the sterile container may be securely closed, the lid must firstly be brought into its closure position before it can be locked relative to the receptacle.

Sterile containers with lids which are either without a rim, have just a very narrow one or rim portions of differing width are frequently subject to the problem of mounting the lid quickly and securely on the receptacle and transferring it to the closure position.

Therefore, it would be advantageous to improve a sterile container and a lid of the type initially described such that it can be quickly and securely mounted on the receptacle and transferred to the closure position.

SUMMARY OF THE INVENTION

This advantage is achieved according to the invention with regard to a lid of the type initially described in that the lid has a mounting aid for mounting the lid on the receptacle, that the mounting aid comprises a plurality of mounting aid elements and that the mounting aid elements each overlap at least one container wall at least partly in the closure position.

This special configuration enables the lid to be placed quickly and securely on the receptacle. The mounting aid elements serve virtually as a guide, this being on account of their at least partial overlap with one or more container walls. The mounting aid elements interact with the container walls even before the lid takes up the closure position, so that the lid and thus the movement are guided during mounting until the closure position is reached. This is particularly of advantage if, in the case of an angular lids, just one rim of the cover plate is initially correctly mounted. The further movement of the lid is guided by the mounting aid elements.

It is favourable for the lid to have a lid rim which comprises a plurality of lid rim portions, for the lid rim to at least partly overlap a plurality of container walls in the closure position and for the lid rim to bear the mounting aid elements. Because the lid rim bears the mounting aid elements, the lid is firstly guided by the mounting aid elements until the lid rim overlaps the container walls and the lid finally takes up the closure position. The mounting aid elements serve as guide aids, so to speak, for mounting and positioning the lid rim on the receptacle.

According to a preferred embodiment of the invention, two non-parallel lid rim portions may meet in a corner region of the lid, and one lid corner or one corner region at most may be disposed between two mounting aid elements. The lid can thus be definitely guided for mounting on the receptacle. It is possible, for example, in the case of a quadrangular lid, to dispose four mounting aid elements along the longitudinal sides of the lid, so that one lid corner is in each case disposed between two mounting aid elements or two mounting aid elements may embrace two diametrically opposite lid corners.

In order to reduce the risk of injury through the lid, the lid corners of the cover plate may be rounded and have a constant or varying radius of curvature.

In order to afford optimum protection against injury, yet at the same time keep the volume of the holding space as large as possible, it is favourable for the outer radius of curvature of the lid to have a value of 4.5 cm at most in the region of the lid corner.

It is of advantage to provide at least two mounting aid elements and dispose the mounting aid elements in each case in a lid corner or a corner region. This arrangement enables the number of mounting aid elements to be minimised, with the risk of injury through the mounting aid elements also being minimised, as these can be integrated into a lid corner or a corner region.

In order to achieve optimum guidance of the lid when mounting the latter on the receptacle, in particular to prevent a movement transversely to a lid edge, it is favourable for a first and a second lid edge, which meet in the lid corner, to form a corner angle, for each mounting aid element to have a rim width over a corner angle region and for the corner angle region to be greater than half the corner angle. The mounting aid element thus forms, for example, a mounting aid which is drawn around a lid corner, so that the lid is guided solely by the mounting aid element during mounting, irrespective of a rim width of a lid rim which in other respects extends right round or is of any desired configuration.

According to a preferred embodiment of the invention, a first lid rim portion may have a maximum first lid rim portion width, a second lid rim portion, which meets the first lid rim portion in a corner region, may have a maximum second lid rim portion width, the smaller width either of the maximum first or second lid rim portion width may define a minimum width, the first and the second lid rim portion may form a corner angle, each mounting aid element may have a rim width over a corner angle region, the corner angle region may be greater than half the corner angle, and the rim width of the corner angle region of the at least two mounting aid elements may be greater than the minimum width or the difference of the two lid rim portion widths. In the case of a lid with lid rim portions of different rim widths, it is consequently possible to form mounting aid elements by drawing the wider of the two lid rim portions which meet at a corner region around the lid corner at least by more than half. On account of this mounting aid element which is thus formed, a movement of the lid transversely to the two lid rim portions meeting in the corner region is thereby prevented when applying or mounting the lid to or on the receptacle, and the lid as a whole is guided into the closure position when mounting takes place.

It is of advantage for the lid to comprise two parallel fist and two parallel second lid rim portions, for the second lid rim portions to be shorter than the first rim portions, and for the lid portion width of the second lid rim portions to be smaller than the lid rim portion width of the fist lid rim portions. The choice of lid rim portion widths of this kind enables, for example on a cuboid container, additional elements, for example carrying handles for the receptacle, to be attached to the narrow front side, while still guaranteeing reliable guidance of the lid during mounting on account of the mounting aid elements.

In order to render the lid sufficiently stable, the lid rim portion width of the second lid rim portions may be approximately half as great as the lid rim portion width of the first lid rim portions.

In order that the lid may be reliably guided during mounting, it is preferable for the corner angle to be 90° or essentially 90° and for the corner angle region to be greater than 45°.

Particularly satisfactory guidance of the lid when mounting the latter on the receptacle is achieved if the corner angle region has at least a value of 75°.

In a further advantageous configuration of the invention the mounting aid may comprise at least one positioning element for introducing top edges of the side walls of the receptacle into a peripheral groove, which is open in the direction of the holding space, of the lid. A seal, for example, may be introduced into the peripheral groove of the lid in order to protect the sterile container against the penetration of germs or bacteria. In order to prevent damage to the seal in the groove, it is desirable to immediately mount the lid in the desired position on the receptacle and transfer it to the closure position. The at least one positioning element, which may be provided in addition to the mounting aid elements or without these, serves this purpose.

The at least one positioning element preferably comprises a rising surface which adjoins a side wall of the peripheral groove. The rising surface enables a top edge of a side wall of the receptacle to be guided along the rising surface until the top edge can enter the groove adjoining the rising surface.

A particularly simple lid structure is obtained if the peripheral groove has an outer and an inner groove side wall, if the outer groove side wall is formed at least partly by the lid rim and if the at least one positioning element comprises a web which projects transversely from the inner groove side wall. The top edge of one side wall of the receptacle is thereby introduced along the web over the inner groove side wall into the groove. The outer groove side wall forms the lid rim, as it were, which may extend right round and have equal or different rim widths.

In order to render a lid more stable, as is particularly advantageous when a lid is made of a plastics material, the lid may have a stabilizing projection extending essentially parallel to the lid rim and the inner groove side wall, at least in portions, and the at least one positioning element may be disposed between the inner groove side wall and the stabilizing projection. The positioning element prevents the top edge of the side wall of the receptacle from entering between the stabilizing projection and the inner groove side wall and becoming caught here. The positioning element at the same time stabilizes both the inner groove side wall and the stabilizing projection through the interposed arrangement.

In order to keep the volume of the holding space as large as possible, the height of the inner groove side wall, starting from the over plate, is smaller than the maximum height of the outer groove side wall and greater than the maximum height of the stabilizing projection.

Furthermore, the advantage initially mentioned is achieved according to the invention with regard to a sterile container of the type initially mentioned in that the lid is formed by one of the lids described above.

In conjunction with the drawings, the following description of a preferred embodiment of the invention serves to provide a detailed illustration.

BRIEF DESCRIPTION OF THE DRAWINGS

FIG. 3 is a sectional view, as a detail, along the line 3-3 in FIG. 2.

DETAILED DESCRIPTION OF THE INVENTION

Figure 1:
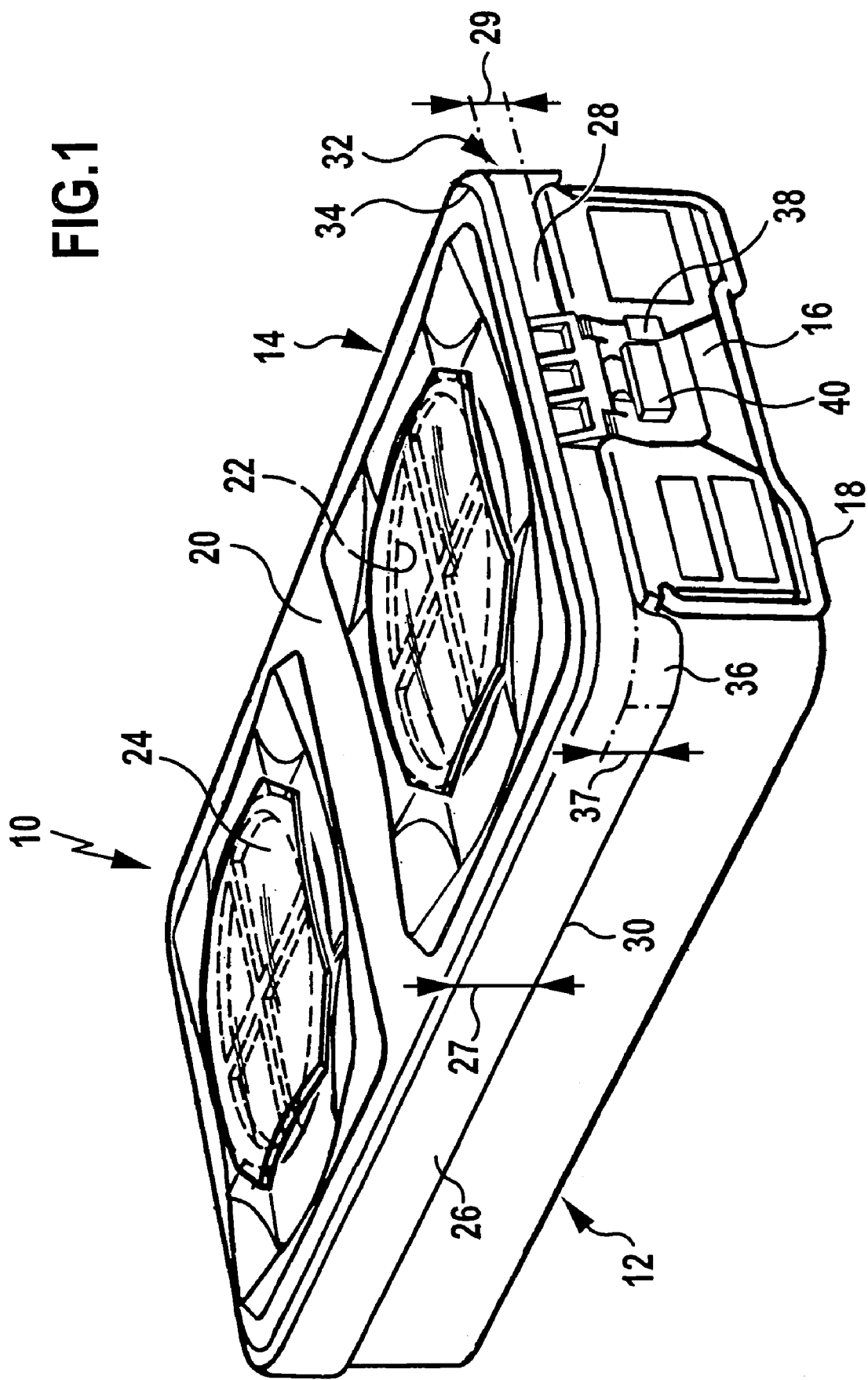
FIG. 1 is a perspective view of a sterile container.

FIG. 1 represents a sterile container which as a whole is given the reference number 10 and comprises a tray 12, which surrounds a cuboid holding space, and a lid 14, which is adapted to close the tray 12. Front sides 16 of the tray 12 are each provided with a pivotably mounted carrying handle 18.

The lid 14 comprises a cover plate 20, into which two gas exchange openings 22 in the form of breakthroughs are worked in a symmetrical arrangement. The case exchange openings 22 are completely covered with a protective lid 24 on an outer side of the lid 14.

Two lid rim portions 26, which extend parallel to one another at the longitudinal sides, and two lid rim portions 28, which extend parallel to one another, together form a lid rim 30. The lid rim portions 26 and 28 meet in four corner regions 32, which in each case enclose a corner 34 of the cover plate 20.

The lid rim portions 28 disposed at the front sides have a rim width 29 which corresponds approximately to half the rim width 27 of the lid rim portions 26 disposed at the longitudinal sides.

Figure 2:
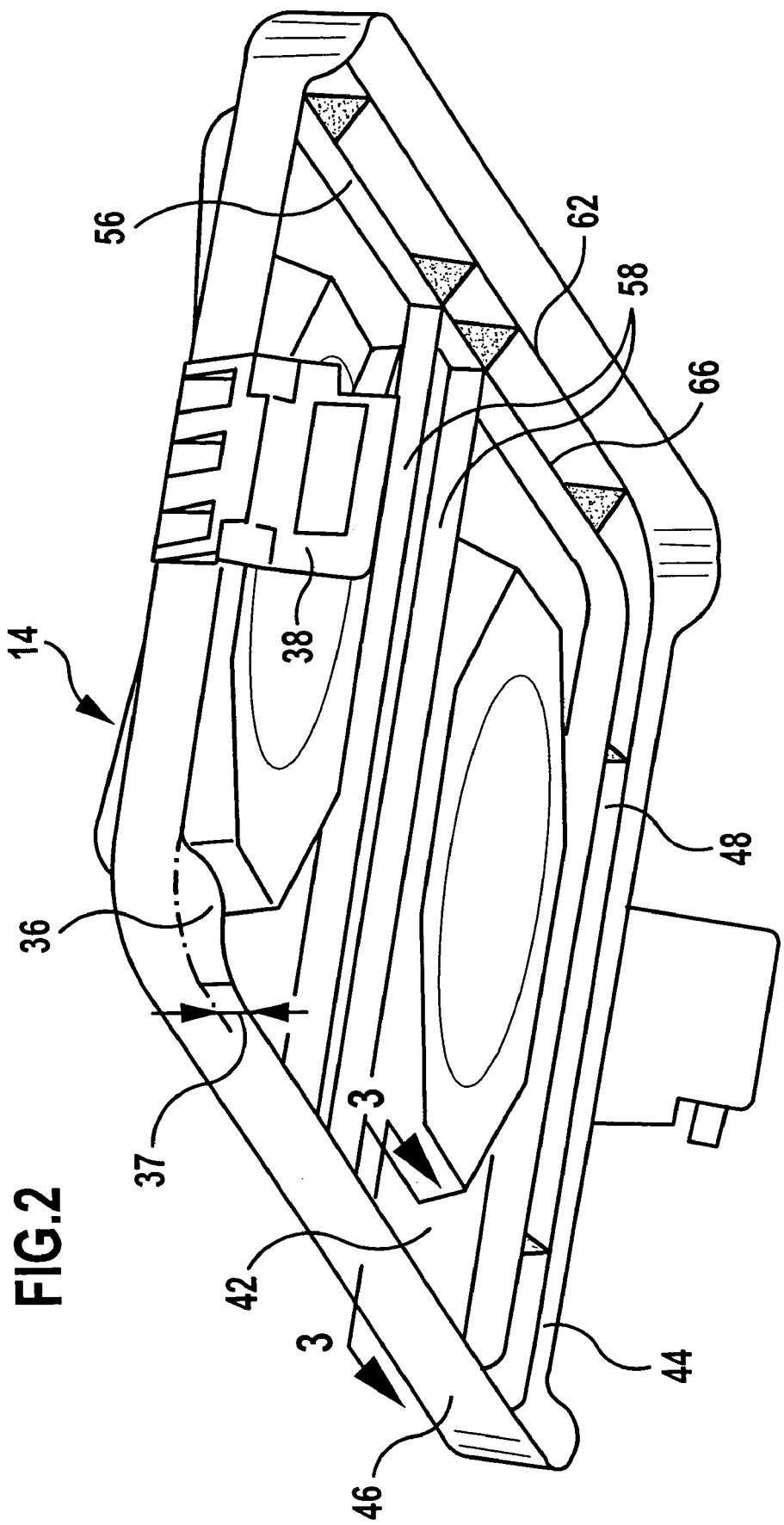
FIG. 2 is a perspective view of an underside of a lid.

In order that the lid 14 may be more easily mounted on the tray 12, mounting aid elements in the form of positioning flaps 36 are disposed in the corner regions 32, these flaps essentially only exhibiting the difference between the rim widths 27 and 29 of the lid rim portions 26 and 28, respectively, disposed at the front sides and longitudinal sides. This is represented both in FIG. 1 and in FIG. 2. The two lid rim portions 26 and 28 meet in the corner regions 32 at an angle of 90°.

Starting from the lid rim portion 26 at the longitudinal side, the positioning flap 36 is drawn over an angular range of approximately 75° around almost the entire corner region 32 and passes without an edge into the lid rim portion 26. Because the corner region 32 of the lid 14 is thus drawn round, the lid, which is mounted on the tray 12 at the front side, can no longer be displaced relative to the tray 12 in the longitudinal direction of the latter, instead being guided as soon as one of the two lid rim portions 26 at the longitudinal sides comes into contact with the tray 12 and until it takes up a closure position. In the closure position a closure clip 38, which is pivotably mounted at the lid rim portion 26 at the front side, can be pivoted by a locking projection 40 and the lid 14 can be locked relative to the tray 12 in the closure position which is represented in FIG. 1.

A peripheral sealing groove 44, which is open in the direction of the tray 12, is disposed at a lid underside 42, this groove comprising an outer-groove side wall 46, which is formed by the four lid rim portions 26 and 28, and an inner groove side wall 48, which extends parallel to the wall 46. The inner groove side wall 48 is slightly narrower than the rim width 27 of the lid rim portions 26 at the front sides. A seal 50, which extends right round and has an essentially circular cross section, is inserted in the sealing groove 44, this seal lying on a top edge 52 of a tray wall 54 in the closure position.

In order to increase the stability of the lid 14, a peripheral projection 56 is disposed parallel to the inner groove side wall 48, which projection is staggered inwards in parallel away from the lid rim 30 in a similar manner and the height of which, viewed from the lid underside 42, is approximately half as great as the inner groove side wall 48. Two frame webs 58, which extend parallel to one another, are additionally disposed at the lid underside 42 parallel to the lid rim portions 28 at the front sides within the projection 56 and so as to connect this to itself.

As represented in FIG. 3, positioning elements in the form of connecting laminae 60 are inserted between the projection 56 and the inner groove side wall 48 in order to reinforce the projection, these laminae defining a plane essentially transverse to the plane which is defined in the region in question by the inner groove side wall. A free edge 62 of the inner groove side wall 48 is connected by way of a lamina edge 64 of the connecting lamina 60 to a free projection edge 66 of the projection 56. The lamina edge 64 forms a rising surface, so to speak, for the top edge 52 of the tray 12 when the top edge 52 is not introduced directly into the sealing groove 44, but is instead mounted on the lamina edge 64.

Four connecting laminae 60 are disposed along portions of the sealing groove 44 at the longitudinal side, and two connecting laminae 60 are disposed along portions of the sealing groove 44 at the front side.

Both the positioning flaps 36 and the connecting laminae 60 together form parts of a mounting aid which facilitates the process of mounting the lid 14 on the pan 12 and transferring the lid into the closure position, in particular also the introduction of the top edge 52 of the tray walls 54 into the sealing groove 44 of the lid 14.

What is claimed:

1. A lid for closing a receptacle, said receptacle having a bottom and side walls that define a holding space, said lid comprising:
    a generally polygonal cover plate adapted to cover a complementary shaped opening of said holding space in a closure position; and
    mounting aids for mounting the lid on said receptacle, the mounting aids comprising:
        a plurality of mounting aid elements extending from respective corners of said cover plate which, in the closure position, each overlap at least partly at least one of said receptacle side walls,
        a plurality of positioning elements for guiding top edges of the receptacle side walls into a peripheral groove of the lid without becoming caught regardless of where the lid is initially placed on said top edges when commencing closure of the container, said groove being open in the direction of the holding space and defined by an inner groove side wall adapted to reside inside said holding space in said closure position and an outer groove side wall adapted to reside outside said holding space in said closure position,
        a peripheral projection spaced inwardly from said inner groove sidewall to provide a channel between said inner groove side wall and said peripheral projection, and
        at least one web connecting a portion of said peripheral projection at one side of said lid to a portion of said peripheral projection at an opposite side of said lid,
        each of said positioning elements spanning said channel and comprising a surface starting from said peripheral
        projection and ending at a distal end of said inner groove side wall for providing said guiding.

2. A lid according to claim 1, wherein:
    the lid has a lid rim which comprises a plurality of lid rim portions,
    the lid rim at least partly overlaps a plurality of container walls in the closure position, and
    the lid rim bears the mounting aid elements.

3. A lid according to claim 1, wherein two non-parallel lid rim portions meet in a corner region of the lid and one lid corner or one corner region at most is disposed between two mounting aid elements.

4. A lid according to claim 1, wherein the lid corners of the cover plate are rounded and have a constant radius of curvature.

5. A lid according to claim 4, wherein the outer radius of curvature of the lid has a value of 4.5 cm at most in the region of the lid corner.

6. A lid according to claim 3, wherein at least two mounting aid elements are provided and the mounting aid elements are in each case disposed in a lid corner or a corner region.

7. A lid according to claim 6, wherein:
    a first and a second lid edge, which meet in the lid corner, form a corner angle,
    each mounting aid element has a rim width over a corner angle region, and
    the corner angle region is greater than half the corner angle.

8. A lid according to claim 3, wherein a first lid rim portion has a maximum first lid rim portion width, a second lid rim portion, which meets the first lid rim portion in a corner region, has a maximum second lid rim portion width, the smaller width either of the maximum first or second lid rim portion width defines a minimum width, the first and the second lid rim portion form a corner angle, each mounting aid element has a rim width over a corner angle region, the corner angle region is greater than half the corner angle and the rim width of the corner angle region of the at least two mounting aid elements is greater than the minimum width or the difference of the two lid rim portion widths.

9. A lid according to claim 8, wherein the lid rim portion width of the second lid rim portions is approximately half as great as the lid rim portion width of the first lid rim portions.

10. A lid according to claim 7, wherein the corner angle is 90° or essentially 90° and the corner angle region is greater than 45°.

11. A lid according to claim 10, wherein the corner angle region has at least a value of 75°.

12. A lid according to claim 1, wherein the height of the inner groove side wall, starting from the cover plate, is smaller than the maximum height of the outer groove side wall.

13. A sterile container comprising:

a receptacle having a bottom and side walls that define a holding space for surgical instruments or material to be held in a sterile state, and a generally polygonal lid for closing a complementary shaped opening of said receptacle, said lid comprising:

a cover plate adapted to cover said holding space in a closure position; and mounting aids for mounting the lid on said receptacle, the mounting aids comprising:

- a plurality of mounting aid elements extending from respective corners of said cover plate which, in the closure position, each overlap at least partly at least one of said receptacle side walls,
- a plurality of positioning elements for guiding top edges of the receptacle side walls into a peripheral groove of the lid without becoming caught regardless of where the lid is initially placed on said top edges when commencing closure of the container, said groove being open in the direction of the holding space and defined by an inner groove side wall adapted to reside inside said holding space in said closure position and an outer groove side wall adapted to reside outside said holding space in said closure position,
- a peripheral projection spaced inwardly from said inner groove sidewall to provide a channel between said inner groove side wall and said peripheral projection, and
- at least one web connecting a portion of said peripheral projection at one side of said lid to a portion of said peripheral projection at an opposite side of said lid,
- each of said positioning elements spanning said channel and comprising a surface starting from said peripheral projection and ending at a distal end of said inner groove side wall for providing said guiding.

14. A container according to claim 13, wherein:

the lid has a lid rim which comprises a plurality of lid rim portions, the lid rim at least partly overlaps a plurality of container walls in the closure position, and the lid rim bears the mounting aid elements.

15. A container according to claim 13, wherein two non-parallel lid rim portions meet in a corner region of the lid and one lid corner or one corner region at most is disposed between two mounting aid elements.

16. A container according to claim 13, wherein the lid corners of the cover plate are rounded and have a constant radius of curvature.

17. A container according to claim 15, wherein at least two mounting aid elements are provided and the mounting aid elements are in each case disposed in a lid corner or a corner region.

18. A container according to claim 15, wherein a first lid rim portion has a maximum first lid rim portion width, a second lid rim portion, which meets the first lid rim portion in a corner region, has a maximum second lid rim portion width, the smaller width either of the maximum first or second lid rim portion width defines a minimum width, the first and the second lid rim portion form a corner angle, each mounting aid element has a rim width over a corner angle region, the corner angle region is greater than half the corner angle and the rim width of the corner angle region of the at least two mounting aid elements is greater than the minimum width or the difference of the two lid rim portion widths.

19. A container according to claim 18, wherein the lid rim portion width of the second lid rim portions is approximately half as great as the lid rim portion width of the first lid rim portions.

20. A container according to claim 13, wherein the height of the inner groove side wall, starting from the cover plate, is smaller than the maximum height of the outer groove side wall.

* * * * *

UNITED STATES PATENT AND TRADEMARK OFFICE
CERTIFICATE OF CORRECTION

PATENT NO. : 7,267,246 B2
APPLICATION NO. : 11/363593
DATED : September 11, 2007
INVENTOR(S) : Eiskant et al.

It is certified that error appears in the above-identified patent and that said Letters Patent is hereby corrected as shown below:

On the title page, the Assignee is corrected to read:
(73) Assignee: AESCULAP AG & Co. KG, Tuttlingen (DE)

Signed and Sealed this

Sixth Day of May, 2008

JON W. DUDAS
*Director of the United States Patent and Trademark Office*